(12) United States Patent
DiBiasio et al.

(10) Patent No.: US 10,039,875 B2
(45) Date of Patent: Aug. 7, 2018

(54) SYSTEMS AND METHODS FOR INCREASING CONVECTIVE CLEARANCE OF UNDESIRED PARTICLES IN A MICROFLUIDIC DEVICE

(71) Applicant: The Charles Stark Draper Laboratory, Inc., Cambridge, MA (US)

(72) Inventors: Christopher DiBiasio, Stoughton, MA (US); Daniel I. Harjes, Acton, MA (US); Joseph L. Charest, Cambridge, MA (US); Jeffrey T. Borenstein, Newton, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 682 days.

(21) Appl. No.: 14/568,666

(22) Filed: Dec. 12, 2014

(65) Prior Publication Data
US 2015/0096936 A1   Apr. 9, 2015

Related U.S. Application Data

(62) Division of application No. 13/739,685, filed on Jan. 11, 2013.

(51) Int. Cl.
*A61M 1/16* (2006.01)
*A61M 1/34* (2006.01)
(Continued)

(52) U.S. Cl.
CPC ................ *A61M 1/16* (2013.01); *A61M 1/34* (2013.01); *B01L 3/502753* (2013.01);
(Continued)

(58) Field of Classification Search
CPC .... A61M 1/34; A61M 1/3403; A61M 1/3413; A61M 1/3417; A61M 1/342;
(Continued)

(56) References Cited

U.S. PATENT DOCUMENTS 4,038,192 A  7/1977 Serur
4,218,321 A  8/1980 Sasaki et al.
(Continued)

FOREIGN PATENT DOCUMENTS

WO   WO-98/09717       3/1998
WO   WO-2011/059786 A1   5/2011
WO   WO-2011/132164    10/2011

OTHER PUBLICATIONS

U.S. Office Action on U.S. Appl. No. 13/739,701 dated Mar. 16, 2016.
(Continued)

*Primary Examiner* — Pranav N Patel
(74) *Attorney, Agent, or Firm* — Christopher J. McKenna; Foley & Lardner LLP

(57) ABSTRACT

A microfluidic device for increasing convective clearance of particles from a fluid is provided. A network of first channels can be separated from a network of second channels by a first membrane. The network of first channels can also be separated from a network of third channels by a second membrane. Fluid containing an analyte can be introduced in the network of first channels. Infusate can be introduced into the network of second channels, and waste-collecting fluid can be introduced into the network of third channels. A pressure gradient can be applied in a direction perpendicular to the direction of fluid flow in the network of first channels, such that the analyte is transported from the network of first channels into the network of third channels through the second membrane.

18 Claims, 10 Drawing Sheets

(51) Int. Cl.
  *B01L 3/00* (2006.01)
  *B01D 63/08* (2006.01)
  *B01D 61/24* (2006.01)
  *B01D 61/28* (2006.01)

(52) U.S. Cl.
  CPC ... *A61M 2205/0244* (2013.01); *B01D 63/082* (2013.01); *B01D 63/088* (2013.01); *B01D 2315/16* (2013.01); *B01L 2200/0631* (2013.01); *B01L 2300/0681* (2013.01); *B01L 2300/0861* (2013.01)

(58) Field of Classification Search
  CPC .... A61M 1/3427; A61M 1/16; A61M 1/1631; B01D 61/24; B01D 61/243; B01D 61/28; B01D 61/30; B01D 61/32; B01D 63/08; B01D 63/081; B01D 63/082; B01D 63/084; B01D 63/085; B01D 63/088
  See application file for complete search history.

(56) References Cited

U.S. PATENT DOCUMENTS

| | | | |
|---|---|---|---|
| 4,789,468 A | 12/1988 | Sirkar | |
| 5,660,722 A * | 8/1997 | Nederlof | A61M 1/3413 210/321.65 |
| 5,730,712 A | 3/1998 | Falkvall et al. | |
| 6,685,809 B1 | 2/2004 | Jacobson et al. | |
| 7,754,077 B1 | 7/2010 | Singh et al. | |
| 2002/0190000 A1* | 12/2002 | Baurmeister | A61M 1/3413 210/650 |
| 2004/0068219 A1* | 4/2004 | Summerton | A61M 1/3413 604/5.01 |
| 2004/0127842 A1* | 7/2004 | Collins | B01D 61/142 604/6.09 |
| 2005/0202557 A1 | 9/2005 | Borenstein et al. | |
| 2008/0000539 A1 | 1/2008 | Bivin | |
| 2008/0093298 A1* | 4/2008 | Browning | A61M 1/16 210/646 |
| 2008/0138596 A1 | 6/2008 | Yoshida et al. | |
| 2008/0251444 A1 | 10/2008 | Fendya et al. | |
| 2008/0318324 A1 | 12/2008 | Chiu et al. | |
| 2010/0032041 A1 | 2/2010 | Diperna | |
| 2010/0285101 A1 | 11/2010 | Moore et al. | |
| 2010/0300882 A1 | 12/2010 | Zhang et al. | |
| 2010/0326916 A1 | 12/2010 | Wrazel et al. | |
| 2011/0082563 A1 | 4/2011 | Charest et al. | |
| 2011/0155667 A1 | 6/2011 | Charest et al. | |
| 2011/0158847 A1 | 6/2011 | Charest et al. | |
| 2011/0290113 A1 | 12/2011 | Borenstein et al. | |
| 2012/0223015 A1 | 9/2012 | Browning et al. | |
| 2014/0197101 A1 | 7/2014 | Harjes et al. | |
| 2014/0197105 A1 | 7/2014 | Dibiasio et al. | |
| 2014/0339161 A1 | 11/2014 | Leonard et al. | |
| 2015/0076067 A1 | 3/2015 | Borenstein et al. | |

OTHER PUBLICATIONS

Office Action dated May 12, 2016 in U.S. Appl. No. 13/739,685.
Office Action dated Dec. 7, 2016 in U.S. Appl. No. 13/739,685.
Office Action dated Nov. 30, 2016 in U.S. Appl. No. 13/739,701.
U.S. Office Action in U.S. Appl. No. 13/739,685 dated Nov. 5, 2013.
International Search Report and Written Opinion dated May 6, 2014 in PCT Application No. PCT/US2014/010683.
Final Office Action in U.S. Appl. No. 13/739,685 dated Jul. 9, 2014.
International Preliminary Report on Patentability dated Jul. 23, 2015 in PCT Application No. PCT/S2014/010683.
International Preliminary Report on Patentability dated Jul. 23, 2015 in PCT Application No. PCT/US2014/010684.
International Search Report and Written Opinion dated Nov. 6, 2015 in PCT Application No. PCT/US2015/046383.
International Search Report and Written Opinion dated May 21, 2014 in PCT Application No. PCT/US2014/010684.
U.S. Office Action in U.S. Appl. No. 13/739,685 dated Nov. 5, 2015.
U.S. Office Action in U.S. Appl. No. 13/739,685 dated Mar. 12, 2015.
U.S. Office Action in U.S. Appl. No. 13/739,701 dated Aug. 14, 2015.
U.S. Office Action in U.S. Appl. No. 13/739,685 dated Jul. 6, 2015.
Vandelnder et al, "Prefusion in Microfluidic Croff-Flow: Separation of White Blood Cells from Whole Blood and Exchange of Medium in a Continuous Flow", Analytical Chemistry, vol. 79, No. 5, pp. 2023-2030, Mar. 1, 2007.
Office Action on U.S. Appl. No. 13/739,685 dated Jun. 1, 2017.
Office Action on U.S. Appl. No. 13/739,685 dated May 12, 2016.
Office Action on U.S. Appl. No. 13/739,701 dated Nov. 30, 2016.
International Search Report and Written Opinion dated May 8, 2017 in PCT Application No. PCT/US2017/018169.
Office Action dated Mar. 23, 2017 in European Patent Application No. 14702347.7.

* cited by examiner

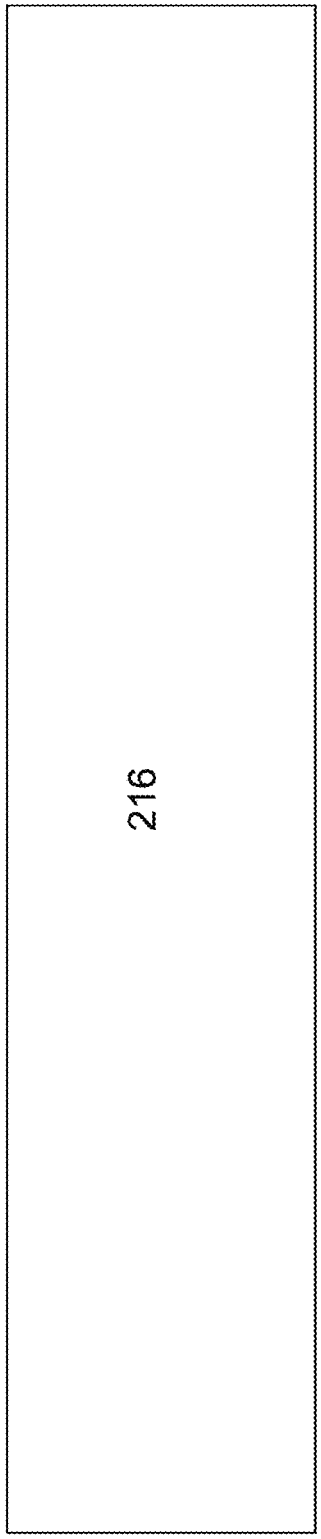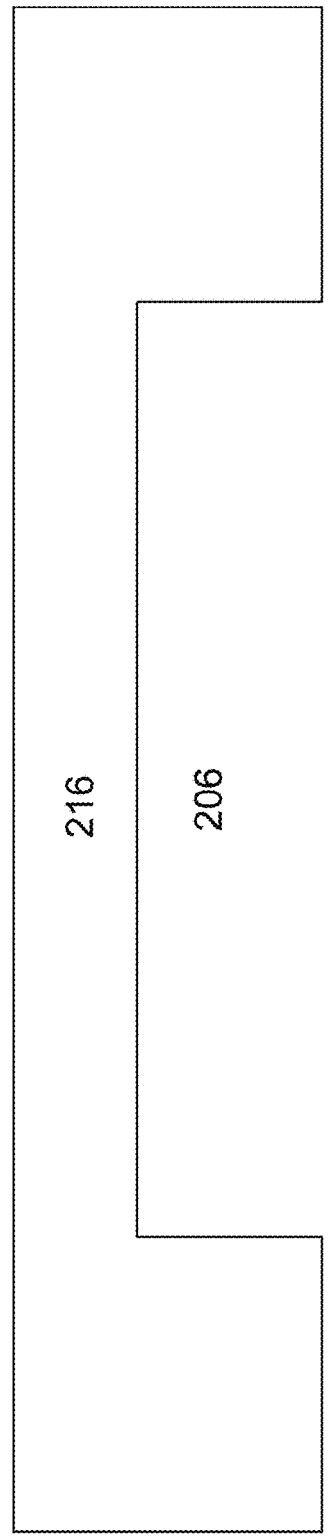

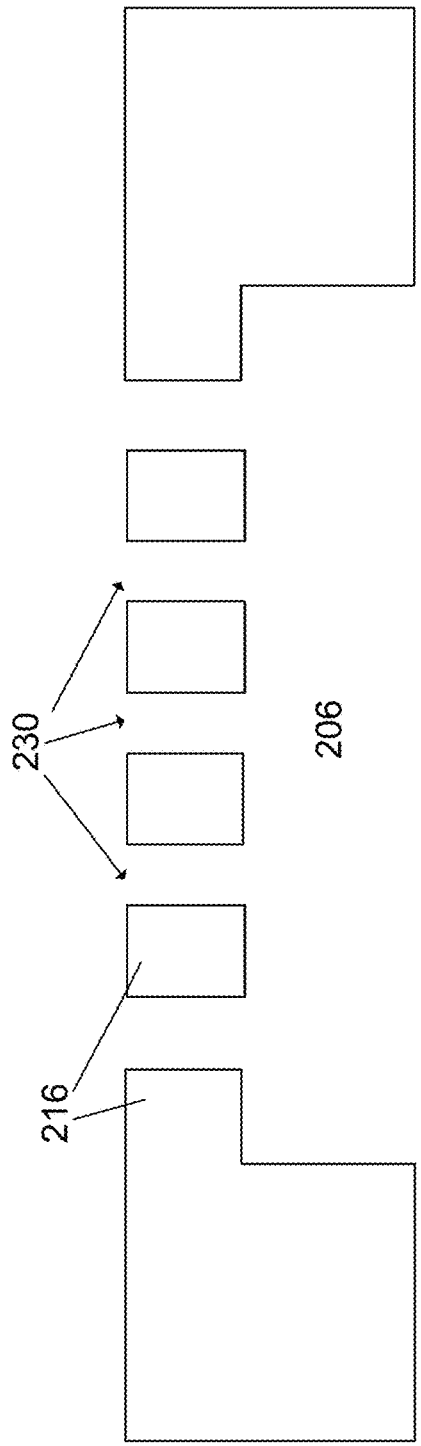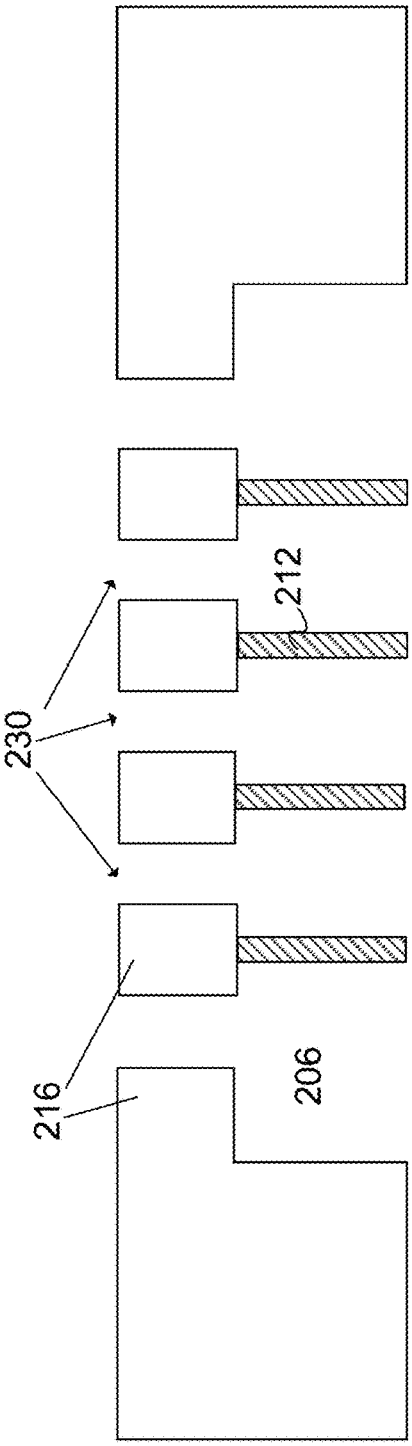

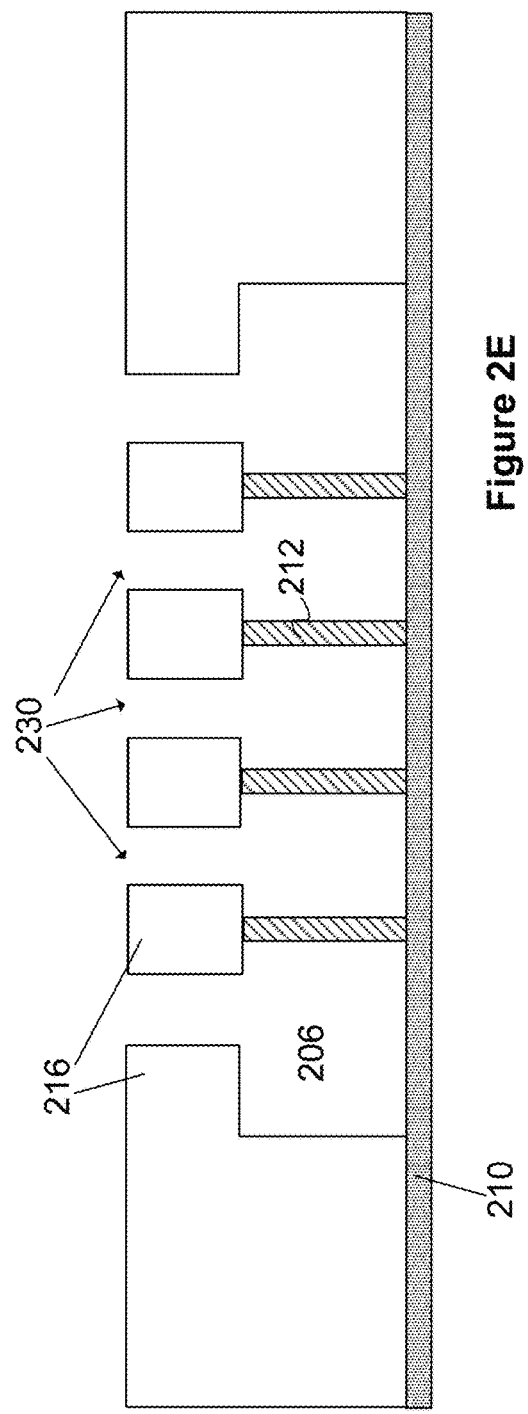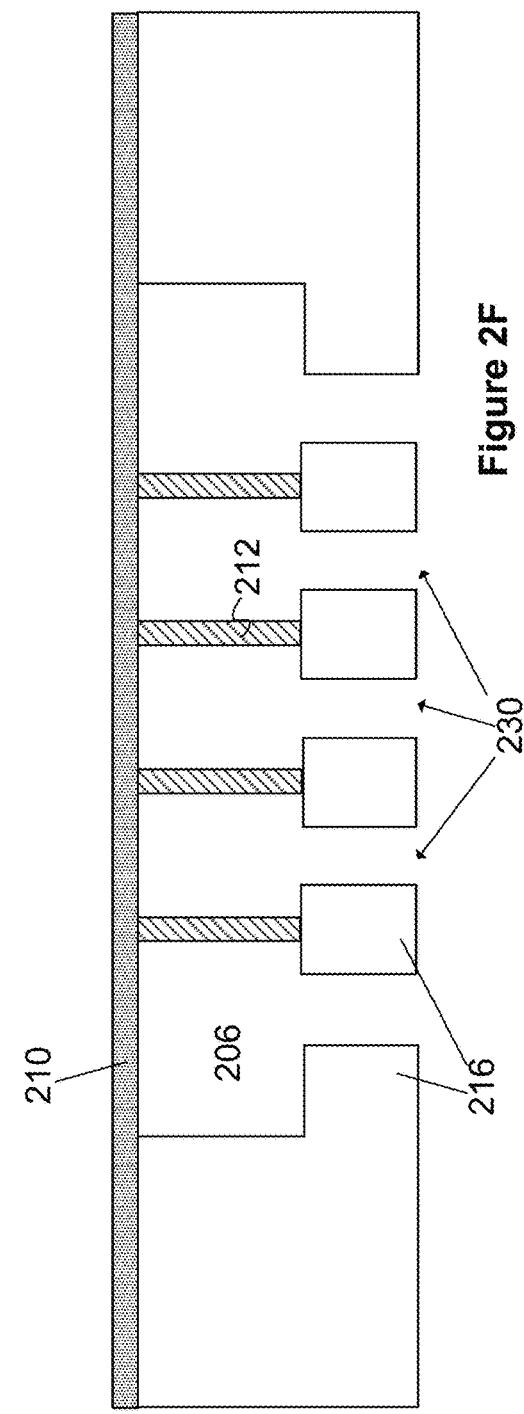

SYSTEMS AND METHODS FOR INCREASING CONVECTIVE CLEARANCE OF UNDESIRED PARTICLES IN A MICROFLUIDIC DEVICE

CROSS REFERENCE TO RELATED APPLICATION

This application is a Divisional of U.S. patent application Ser. No. 13/739,685, filed on Jan. 11, 2013, the content of which is incorporated by reference herein in its entirety.

BACKGROUND

A dialysis device contains a series of fluid channels separated by a permeable membrane. Convective clearance of solutes from blood in the device is determined by the transmembrane pressure in the device. Typically, the fluid in adjacent channels flows in opposite directions and the channels have a non-linear fluid volume profile along their lengths. Increasing the convective clearance requires decreasing the fluid volume in the channel carrying blood, which can result in an unsafe hematocrit level in the channel. Therefore, it is desirable to increase the amount of convective clearance within a compact dialysis device while maintaining safe hematocrit levels throughout the blood channel.

SUMMARY OF THE INVENTION

Aspects and implementations of the present disclosure are directed to a device for increasing convective transport of solutes in blood within a dialysis system.

At least one aspect is directed to a microfluidic device. The microfluidic device includes a first network of channels having a plurality of First Channels. Each First Channel has a height in the range of about 50 microns to about 500 microns, a width in the range of about 50 microns to about 1.5 millimeters, and a length in the range of about 3 centimeters to about 20 centimeters. The microfluidic device includes a second network of channels having at least one Second Channel complementary to one or more of the First Channels. The microfluidic device includes a first filtration membrane separating the one or more First Channels from the at least one Second Channel. The microfluidic device includes a third network of channels having at least one Third Channel complementary to one or more of the First Channels. The microfluidic device includes a second filtration membrane separating the one or more First Channels from the at least one Third Channel.

In some implementations, the microfluidic device includes a fluid introduction device configured to flow fluid in the at least one Second Channel. The fluid can be flowed in a direction perpendicular to a direction of fluid flow in the one or more First Channels, such that fluid flows from the at least one Second Channel into the one or more First Channels and from the one or more First Channels into the at least one Third Channel.

In some implementations, the microfluidic device can include at least one structural support within at least one of the First, Second, or Third Channels. The structural support can be configured to limit the deformation of the first or second membrane towards the one or more First Channels or the at least one Second Channel. The structural support can be a porous mesh made from ceramic, carbon, or polymer. The structural support can also be a post or ridge placed within the one or more First Channels, the at least one Second Channel, or the at least one Third Channel.

In some implementations, the one or more First Channels of the microfluidic device are defined in part by a substantially planar substrate. The at least one Second Channel and the at least one Third Channel can be configured to allow fluid to flow in a direction perpendicular to the plane of the substrate. In some implementations, the microfluidic device can be configured such that the volume of fluid in the one or more First Channels is substantially constant along its length.

In some implementations, the pore size of the second membrane is selected to allow clearance of particles with a molecular weight of no more than about 60 kDa. The one or more First Channels can be configured to receive a net infusion of fluid from the at least one Second Channel through the first membrane and can be further configured to provide a net outflow of fluid into the at least one Third Channel through the second membrane. In some implementations, the device is configured such that a hematocrit profile in the one or more First Channels is selectably controllable by an operator of the device when blood is flowed through the one or more First Channels.

In some implementations, the microfluidic device is configured such that hematocrit is substantially constant throughout the one or more First Channels when blood is transported through the one or more First Channels. In some implementations, the one or more First Channels are configured such that fluid flow in the one or more First Channels is substantially laminar. In some implementations, the one or more First Channels are configured to maintain wall shear rates in the range of 300-3000 inverse seconds when blood is transported through the one or more First Channels. In some implementations, the microfluidic device includes an anticoagulant coating on the inner surfaces of the one or more First Channels.

At least one aspect is directed to a method for filtering a first liquid containing an analyte to provide a filtered liquid containing less analyte than the first liquid. The method can include introducing the first liquid into an inlet of one or more First Channels, each First Channel having a height in the range of about 50 microns to about 500 microns, a width in the range of about 50 microns to about 900 microns, and a length in the range of about 3 centimeters to about 20 centimeters. The method can include introducing an infusate into at least one Second Channel complementary to the one or more First Channels in a direction perpendicular to the direction of fluid flow in the one or more First Channels, such that at least some of the infusate flows from the at least one Second Channel through a first membrane and into the one or more First Channels. The method can include introducing waste-collecting fluid into at least one Third Channel complementary to the one or more First Channels such that at least some of the analyte of the first liquid is transported through a second membrane into the at least one Third Channel. The method can include collecting the filtered solution from an outlet of one or more of the First Channels.

In some implementations, introducing the first liquid includes introducing blood. The blood can be extracted from a patient and can filtered blood can be returned to the patient. The blood and the infusate can be introduced such that hematocrit of the blood is substantially constant throughout the one or more First Channels. The blood can be introduced such that a fluid shear rate in the one or more First Channels is within a range of about 300 inverse seconds to about 3000 inverse seconds. The one or more First Channels can include an anticoagulant coating on its inner walls.

In some implementations, the first liquid and the infusate can be introduced such that the volume of fluid in each of the one or more First Channels is substantially constant along its length. The first liquid and the infusate can be introduced such that fluid flow in the one or more First Channels is substantially laminar. In some implementations, the first liquid and the infusate can be introduced such that a pressure in the at least one Second Channel is greater than a pressure in the one or more First Channels, and the pressure in the one or more First Channels is greater than a pressure in the at least one Third Channel.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing.

FIGS. 2A-2H depict the device of FIG. 1A at various points in the manufacturing process, according to an illustrative implementation.

DESCRIPTION OF CERTAIN ILLUSTRATIVE IMPLEMENTATIONS

Following below are more detailed descriptions of various concepts related to, and implementations of, a device for increasing convective transport of solutes in blood within a dialysis system. The various concepts introduced above and discussed in greater detail below may be implemented in any of numerous ways, as the described concepts are not limited to any particular manner of implementation. Examples of specific implementations and applications are provided primarily for illustrative purposes.

Figure 1A:
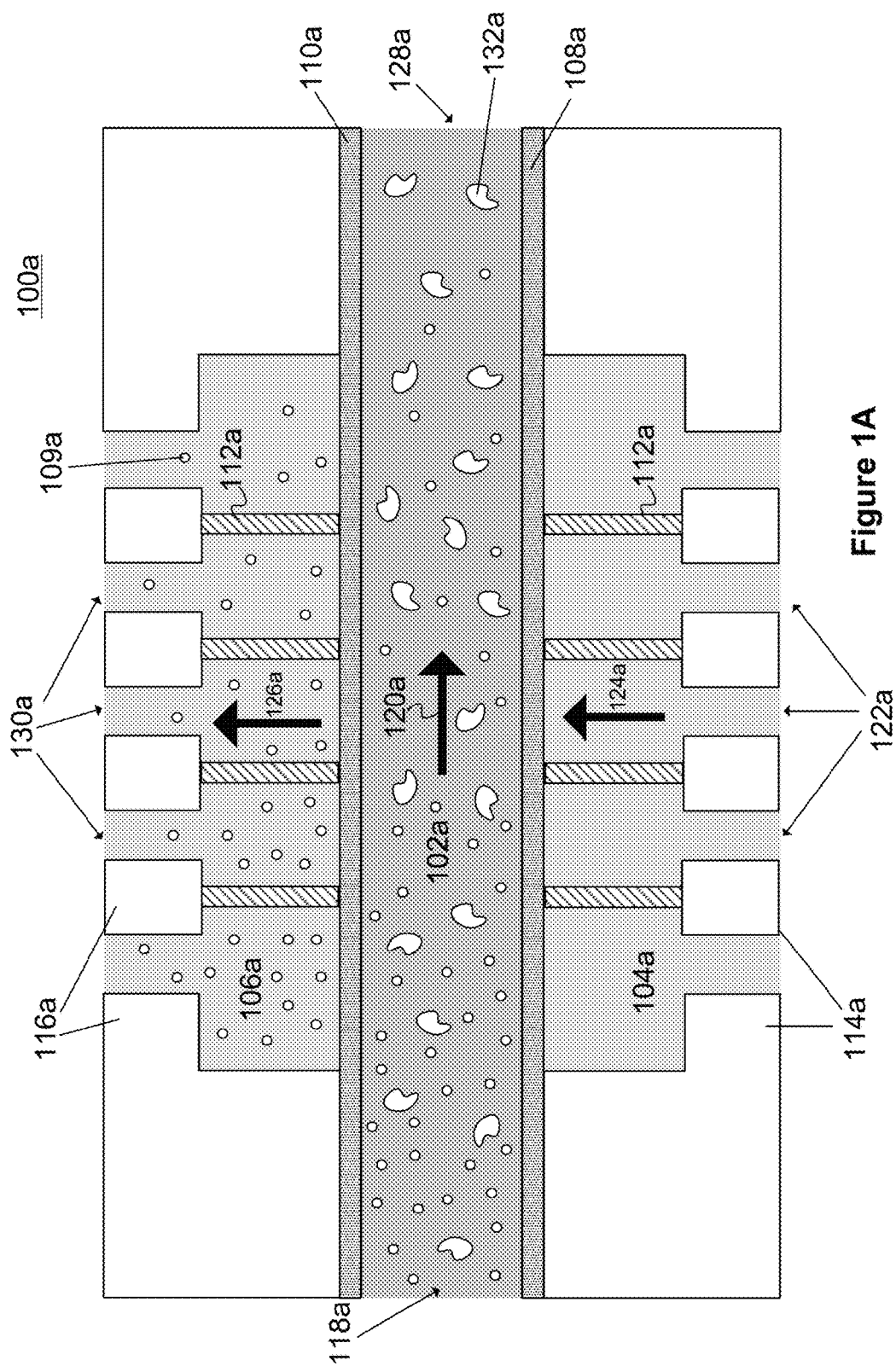
FIG. 1A is a cross-sectional view of a first microfluidic convective clearance device for use in hemofiltration, according to an illustrative implementation.

FIG. 1A is a cross-sectional view of a first microfluidic convective clearance device 100a for use in hemofiltration The convective clearance device 100a includes a blood channel 102a, an infusate channel 104a, and a waste channel 106a. A first membrane 108a separates the blood channel 102a from the infusate channel 104a, and a second membrane 110a separates the blood channel 102a from the waste channel 106a. The infusate channel 104a and the waste channel 106a also include structural supports 112a.

The blood channel 102a has a depth in the range of about 50 microns to about 500 microns, a width in the range of about 50 microns to about 900 microns, and a length in the range of about 3 centimeters to about 20 centimeters. The infusate channel 104a is defined by an infusate substrate 114a and the waste channel 106a is defined by a waste substrate 116a. The substrates 114a and 116a can be made from a polystyrene, polycarbonate, polyimide, polysulfone, polyethersulfone, acrylic, or cyclic olefin copolymer (COC), biodegradable polyesters, such as polycaprolactone (PCL), soft elastomers such as polyglycerol sebacate (PGS), or other thermoplastics. The substrates may alternatively be made of polydimethylsiloxane (PDMS), poly(N-isopropylacrylamide), or nanotubes or nanowires formed from, for example, carbon or zinc oxide.

The upper and lower walls of the blood channel 102a are defined by the membranes 110a and 108a, respectively. In some implementations, the side walls of the blood channel can be made from a substrate material similar to the substrates 114a and 116a. The blood channel 102a can be coated with cytophilic or cytophobic materials to promote or prevent the growth of cells, such as vascular endothelial cells, in the channels. The blood channel 102a may also be coated with an anticoagulant to help prevent clotting of the blood. In some implementations, the anticoagulant is applied to the substrate walls of the blood channel 102a, but not to the walls defined by the membranes 108a and 110a.

The convective clearance device 100a is designed for use in hemofiltration. The blood channel 102a, the infusate channel 104a, and the waste channel 106a are configured such that a relatively large surface area of the fluid flowing through the channels is exposed to the membranes 108a and 110a. In some implementations, the channels 100a, 104a, and 106a can have rectangular cross-sections, with a relatively large fluid interface at the membranes 108a and 110a, to promote fluid communication between the blood channel 102a, the infusate channel 104a, and the waste channel 106a. The channels 102a, 104a, and 106a can alternatively have semicircular cross sections. In other implementations, the channels 102a, 104a, and 106a may have any other type of cross section, such as a substantially rectangular cross-section with rounded corners, or an irregularly shaped cross-section.

Blood is introduced into an inlet 118a of the blood channel 102a and flows along the length of the blood channel 102a in the direction indicated by arrow 120a. Infusate (e.g., saline) is simultaneously introduced into the infusate channel 104a through inlets 122a. A transverse pressure is applied to the infusate channel 104a and the waste channel 106a, causing fluid in these channels to flow in the directions indicated by the arrows 124a and 126a, respectively. As blood flows through the blood channel 102a, the transverse pressure gradient causes an infusion of infusate to flow from the infusate channel 104a, through the membrane 108a, and into the blood channel 102a. The infusion of infusate increases the total amount of fluid in the blood channel 102a, resulting in an increased pressure in the blood channel 102a. Therefore, fluid from the blood channel 102a, including plasma, urea, and other waste particles, such as particle 109a, is forced into the waste channel 106a through the membrane 110a. Cleansed blood can then be collected from an outlet 128a of the blood channel 102a. Waste-collecting fluid passes out of the convective clearance device 100a through outlets 130a in the waste collecting channel, and can then be filtered and recirculated back to the inlets 122a of the infusate channel 104a. Blood and infusate can be introduced in such a way as to maintain substantially laminar flow in the blood channel 102a. In some implementations, the infusate channel 104a and the waste channel 106a can be reservoirs or fluid baths whose volume is significantly larger than the volume of the blood channel 102a.

The membrane 110a can be configured to allow clearance of particles having a molecular weight of less than about 60 kDa. Larger particles exemplified by particle 132a, such as blood cells, can remain within the blood channel. The membrane 108a can be identical to the membrane 110a.

However, in some implementations, the membrane 108a can have pore sizes that are significantly smaller than the pore sizes of the membrane 110a, because it is only necessary to allow fresh infusate to pass through the membrane 108a. For example, smaller pore sizes may be selected to prevent the introduction of impurities into the blood channel 102a while still allowing infusate to flow into the blood channel 102a. In other implementations, desirable solutes may be introduced into the infusate channel 104a, and the membrane 108a can be configured to allow the desirable solutes to pass into the blood channel 102a. The membrane 108a can be made from an impermeable material into which pores have been fashioned, for example by a laser etching process. Alternatively, the membrane 108a can be constructed from a naturally porous material.

The pressure gradient indicated by the arrows 124a and 126a is substantially constant throughout the lengths of the infusate channel 104a and the waste channel 106a. For example, substantially constant pressure can be achieved by positioning a number of inlets 122a along the length of the infusate channel 104a. Similarly, a number of outlets 130a can be positioned along the length of the waste-collecting channel 106a. This allows the blood channel 102a to experience a simultaneous infusion of fluid from the infusate channel 104a and outflow of fluid to the waste channel 106a, which results in a substantially constant volume of blood along the length of the blood channel 102a. By contrast, in typical hemodialysis devices, forward filtration occurs along a portion of the length of the device, and back filtration occurs along a separate portion of the device, resulting in a varying fluid volume profile along the length of the device. Achieving increased convective clearance in these types of devices requires a larger variance of the volume of blood along the length of the device, which can lead to unsafe hematocrit levels.

Hematocrit in the blood channel 102a is preferably maintained within an acceptable range in order to ensure blood health. The substantially constant volume of fluid maintained in the blood channel 102a causes a substantially constant hematocrit level in the blood channel 102a. Therefore the amount of convective clearance achieved in the convective clearance device 100a can be increased without significantly increasing the risk of unsafe hematocrit levels. In some implementations, the amount of convective clearance is proportional to the magnitude of the transverse pressure gradient indicated by arrows 124a and 126a. As discussed above, increasing the infusion of fluid from the infusate channel 104a to the blood channel 102a results in an increased outflow of fluid form the blood channel 102a to the waste channel 106a, while preserving the volume of fluid in the blood channel 102a. Other hemodialysis devices typically require increased channel lengths and increased residence time of fluid in the channels in order to increase the amount of convective clearance. The convective clearance device 100a can therefore be used to achieve significantly higher levels of convective clearance without a need for increasing the overall size of the convective clearance device 100a.

The transverse pressure gradient may expose the membranes 108a and 110a to stresses that can cause the membrane 108a to deform towards the blood channel 102a and can cause the membrane 110a to deform towards the waste channel 106a. To prevent significant deformation of the membranes 108a and 110a, the infusate channel 104a and the waste-collecting channel 106a can include structural supports 112a. The structural supports 112a can span the width of the infusate channel 104a and the waste-collecting channel 106a, and can be attached to the membranes 108a and 110a to hold them in place against the force of the fluid pressure gradient indicated by arrows 124a and 126a. In other implementations, the structural supports 112a can substantially fill the volume of the infusate channel 104a and the blood channel 106a to provide rigidity to the channels 104a and 106a and reduce deformation of the membranes 108a and 110a. For example, the structural supports 112a can be porous mesh structures made from ceramic, carbon, polymer, or other materials. The structural supports 112a can also be posts or ridges inserted into the blood channel 102a, the infusate channel 104a, or the waste-collecting channel 106a. To prevent the obstruction of fluid flow in the infusate channel 104a and the waste-collecting channel 106a, the structural supports 112a can be selected to have pore sizes that are larger than the pore sizes of the membranes 108a and 110a, so that the clearance of particles from the fluids is controlled only by the pore sizes of the membranes 108a and 110a.

Figure 1B:
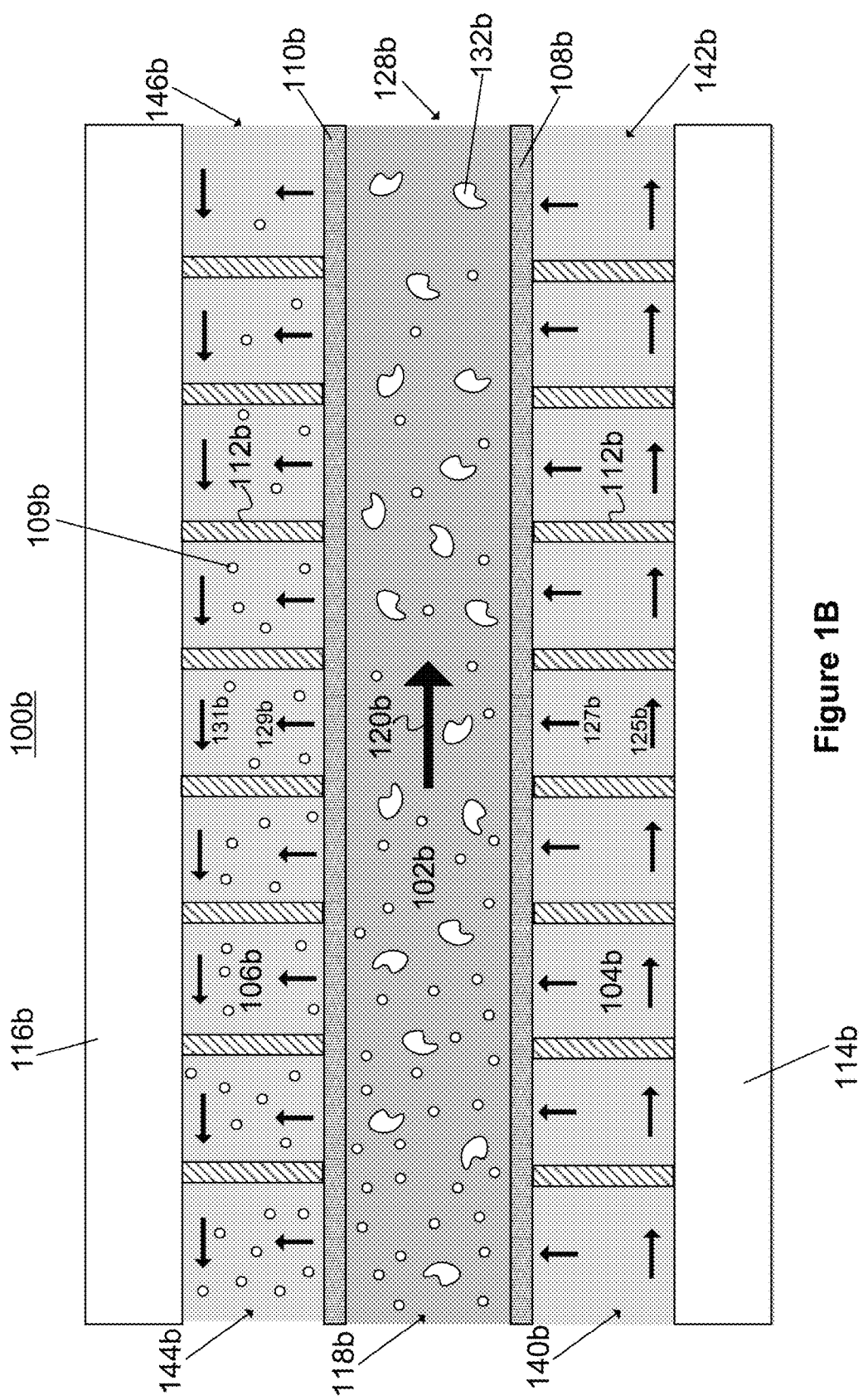
FIG. 1B is a cross-sectional view of a second microfluidic convective clearance device for use in hemofiltration, according to an illustrative implementation.

In some implementations, a microfluidic convective clearance device similar to the device 100a can be configured such that only a portion of the fluid in the infusate channel and waste channel flows perpendicular to the flow of fluid in the blood channel, while the remaining portion of fluid in the infusate channel and waste channel flows parallel to the flow of fluid in the blood channel. An example of such a device is shown in FIG. 1B FIG. 1B is a cross-sectional view of a second microfluidic convective clearance device 100b for use in hemofiltration, according to an illustrative implementation. The device 100b includes many of the features of the device 100a shown in FIG. 1A. For example, the device 100b includes a blood channel 102b, an infusate channel 104b, and a waste-collecting channel 106b. The channels are defined by walls made from substrate materials 114b and 116b and membranes 108b and 110b, and can include structural supports 112b. Fluid can be introduced into an inlet 140b of the infusate channel 104b. The pressure in the infusate channel 104b causes some of the fluid to pass through the membrane 108b and into the blood channel 102b, in the direction shown by the arrow 127b. The remaining portion of the fluid in the infusate channel 104b can travel parallel to the blood channel 102b along the length of the channel 104b, as shown by the arrow 125b, and can be collected at an outlet 142b.

The infusion of fluid from the infusate channel 104b into the blood channel 102b increases the pressure in the blood channel 102b, causing some of the fluid in the blood channel 102b to pass into the waste-collecting channel 106b through the membrane 110b, in the direction shown by the arrow 129b. Undesired particles, such as particle 109b, can also pass through the membrane 110b into the waste-collecting channel 106b. In some implementations, additional waste-collecting fluid can be introduced at an inlet 146b of the waste-collecting channel 106b, causing fluid within the waste-collecting channel 106b to flow in the direction shown by arrow 131b. Waste-collecting fluid can be collected from the outlet 144b, and purified blood can be collected from the outlet 128b as the blood flows along the blood channel 102b in the direction shown by the arrow 120b. In some other implementations, the waste-collecting fluid can be introduced such that the fluid in the waste-collecting channel flows in a direction opposite the direction shown by arrow 131b.

Figure 1C:
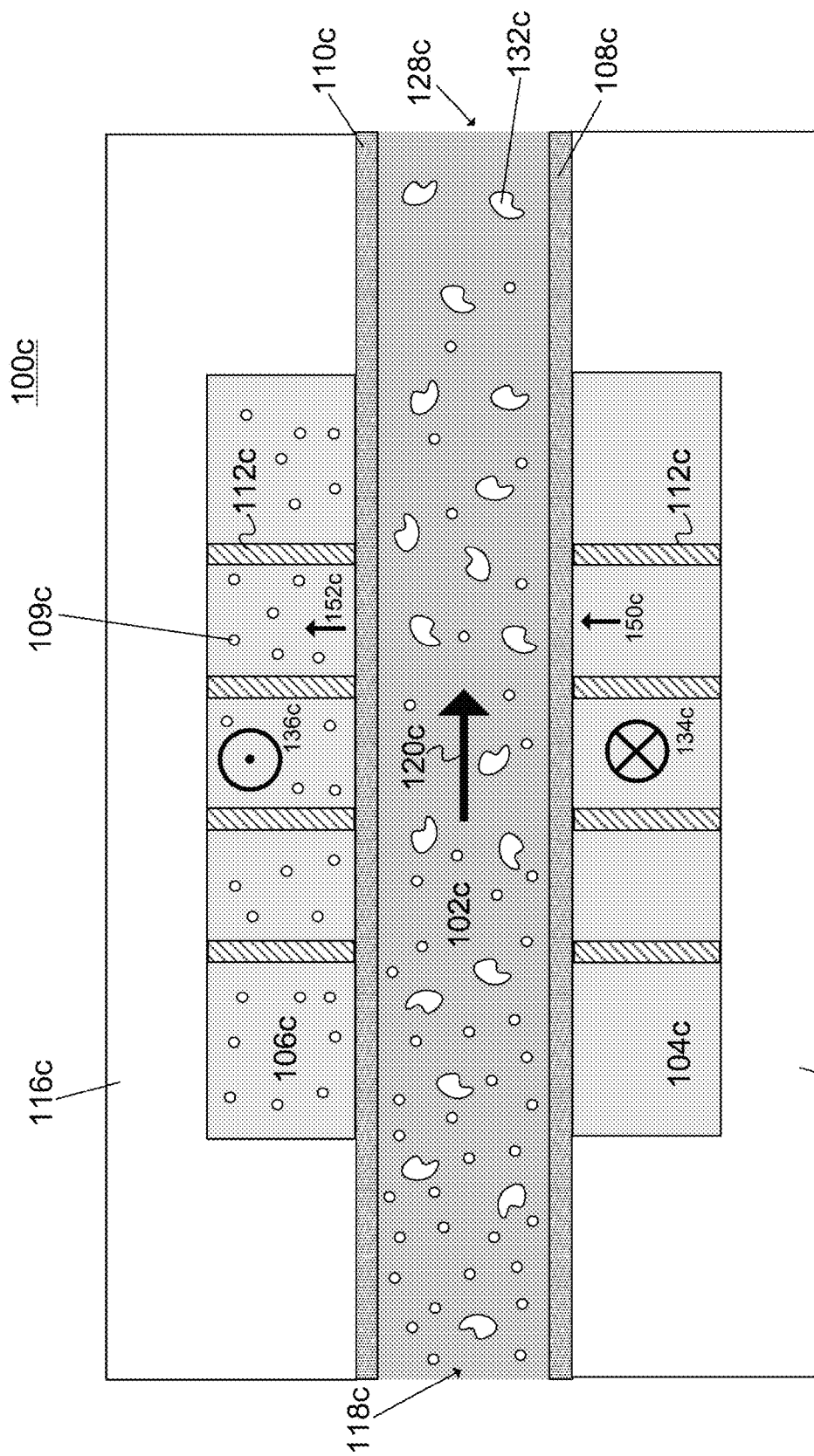
FIG. 1C is a cross-sectional view of a third microfluidic convective clearance device for use in hemofiltration, according to an illustrative implementation.

FIG. 1C is a cross-sectional view of a third microfluidic convective clearance device 100c for use in hemofiltration, according to an illustrative implementation. The device 100c includes many of the features of the device 100a shown in FIG. 1A. For example, the device 100c includes a blood channel 102c, an infusate channel 104c, and a waste-collecting channel 106c. The channels are defined by walls made from substrate materials 114c and 116c and membranes 108c and 110c, and can include structural supports 112c. Unlike the device 100b of FIG. 1B in which the an infusate channel 104b and a waste collecting channel 106b run parallel to the blood channel 102b, the infusate channel 104c and waste-collecting channel 106c of the device 100c are oriented perpendicular to the blood channel 102c.

Fluid can be introduced into an inlet of the infusate channel 104c in the direction shown by the vector 134c (i.e, directed into the page). The pressure in the infusate channel 104c causes some of the fluid to pass through the membrane 108c and into the blood channel 102c, in the direction shown by the arrow 150c. The remaining portion of the fluid in the infusate channel 104c can travel along the length of the channel 104c, in the direction of the vector 134c, and can be collected at an outlet.

The infusion of fluid from the infusate channel 104c into the blood channel 102c increases the pressure in the blood channel 102c, causing some of the fluid in the blood channel 102c to pass into the waste-collecting channel 106c through the membrane 110c, in the direction shown by the arrow 152c. Undesired particles, such as particle 109c, can also pass through the membrane 110c into the waste-collecting channel 106c. In some implementations, additional waste-collecting fluid can be introduced at an inlet of the waste-collecting channel 106c, causing fluid within the waste-collecting channel 106c to flow in the direction shown by vector 136c (i.e., out of the page). Waste-collecting fluid can be collected from an outlet of the waste-collecting channel, and purified blood can be collected from the outlet 128c of the blood channel 102c as the blood travels along the blood channel 102c in the direction shown by arrow 120c. In some other implementations, the waste-collecting fluid can be introduced such that the fluid in the waste-collecting channel flows in a direction opposite the direction shown by vector 136c (i.e., parallel to the direction of fluid flow in the infusate channel 104c.

FIGS. 2A-2F depict the device of FIG. 1A at various points in the manufacturing process. FIG. 2A shows a rectangular block of substrate material 216. The substrate material can be used to form either the infusate channel or the waste-collecting channel of FIG. 1A, as both of these channels are very similar. Therefore, the processes discussed in connection with the manufacture of either channel will also be useful in the manufacture of the other. The substrate material 216 can be any of the materials described above in connection with the substrates used in the device of FIG. 1A, such as thermoplastics, biodegradable polyesters, or nanotubes or nanowires formed from, for example, carbon or zinc oxide. The substrate material 216 can be a solid block whose dimensions are selected to provide sufficient volume to form the infusate channel or waste collecting channel of FIG. 1A.

FIG. 2B shows a cross-sectional view of the substrate 216 of FIG. 2A after it has been hollowed out to form a channel 206. For example, the channel 206 can be used as the infusate channel or the waste-collecting channel of FIG. 1A. The channel 206 can be created in the substrate 216 by any method of material removal, such as an etching or milling process. The result is the hollow channel 216 suitable for carrying infusate or waste-collecting fluid, surrounded on three sides by the substrate material 216. The fourth side of the channel will be formed by a membrane, so the substrate material 216 is completely removed from this side.

FIG. 2C shows a cross-sectional view of the substrate 216 and the channel 206. Also shown are openings 230 leading into the channel 206. The openings 230 can be used as the infusate inlets or waste fluid outlets described in FIG. 1A. In some implementations, the openings 230 are positioned evenly across the surface of the substrate 216, to facilitate an even pressure gradient along the length of the channel 206. Although five openings 216 are shown in FIG. 2C, any number of openings 216 can be present. In some implementations, the openings can be created by a chemical or laser etching, drilling, or milling process in which material is removed from the surface of the substrate 206. The shape of the openings can be circular, rectangular, or any other shape suitable for introducing fluid into the openings (e.g., into the inlets of the infusate channel of FIG. 1A) or extracting fluid from the openings (e.g., from the outlets of the waste-collecting channel of FIG. 1A).

FIG. 2D shows a cross-sectional view of the substrate material 216, channel 206, and openings 230. Also shown in FIG. 2D are structural supports 212 coupled to the substrate 216. The structural supports 212 are intended to reinforce the structural integrity of the channel 206 and to prevent deformation of a membrane that will be added later in the process, so the structural supports 212 are preferably made from a substantially rigid material such as a polymer or a metal. As shown in FIG. 2D, the structural supports can be aligned with the direction of fluid flow in the channel 206 (see arrows 124a and 126a of FIG. 1A), in order to reduce interference with the flow of infusate or waste-collecting fluid in the channel 206. In other implementations, the structural supports 212 can occupy a substantial portion of the channel 206. For example, the structural supports 212 can be made from a porous material that allows fluid to flow through the channel 206. The structural supports 212 can be coupled to the substrate 216 by a mechanical joint or by a medical grade adhesive suitable for use in a fluid channel.

FIG. 2E shows a cross-sectional view of the substrate 216 configured as in FIG. 2D, with the addition of a membrane 210. The membrane 210 can be used as either of the membranes 108a or 110a of FIG. 1A. In some implementations, the membrane 210 is selected to allow clearance of particles having a molecular weight smaller than about 60 kDa. The membrane 210 is coupled to the structural supports 210 in order to prevent the membrane 210 from deforming under the pressure of the fluid flowing through the channel 206. The membrane 210 can be joined to the structural supports 212 by a mechanical fastener or by an adhesive.

FIG. 2F shows the features of the infusate channel of FIG. 1A. As discussed above, the elements shown in FIG. 2E can be used to form either the infusate channel or the waste-collecting channel of FIG. 1A. Therefore, structure of FIG. 2F can be manufactured by repeating the process described in connection with FIGS. 2A-2E to produce a second structure. The structure of FIG. 2F is similar to the structure shown in FIG. 2E, but rotated 180 degrees such that the openings 230 of FIG. 2F are opposed to the openings of FIG. 2E.

Figure 2G:
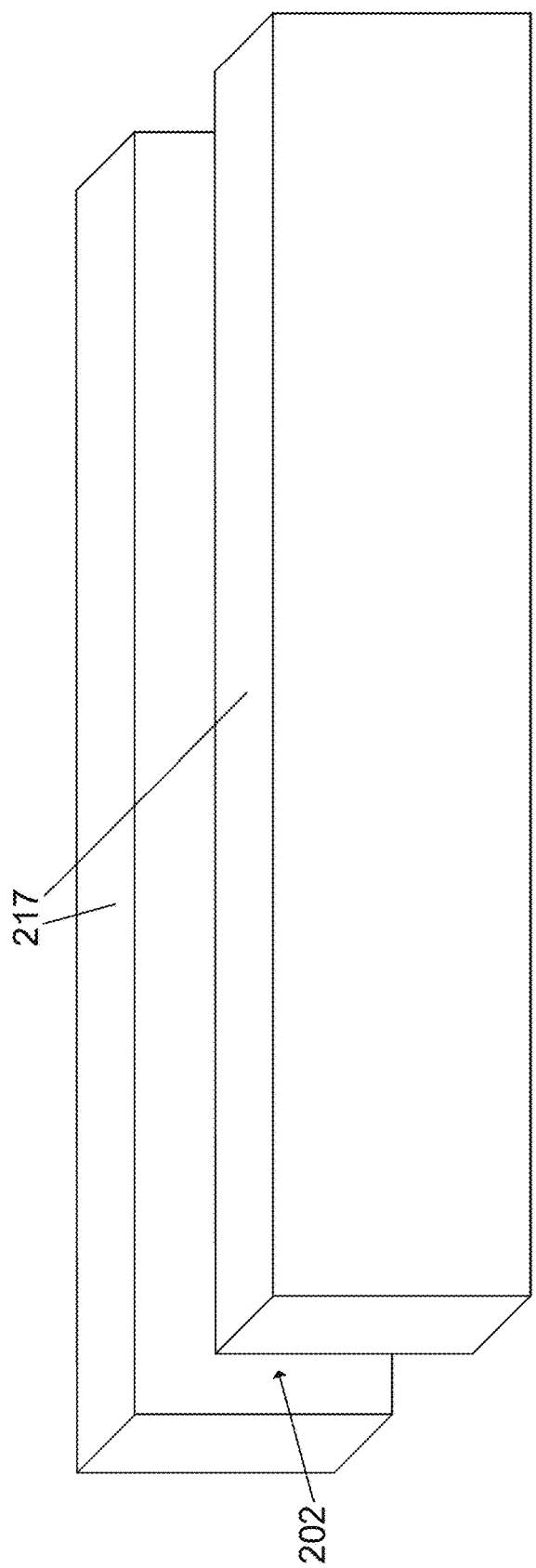

FIG. 2G shows a pair of substrate walls 217. The substrate walls are parallel to each other and define the side walls of a channel 202, which can be used as the blood flow channel of FIG. 1A. The channel 202 is open on its top and bottom sides at this step in the process, but will eventually be defined by the membranes 210 as shown in FIG. 2H.

Figure 2H:
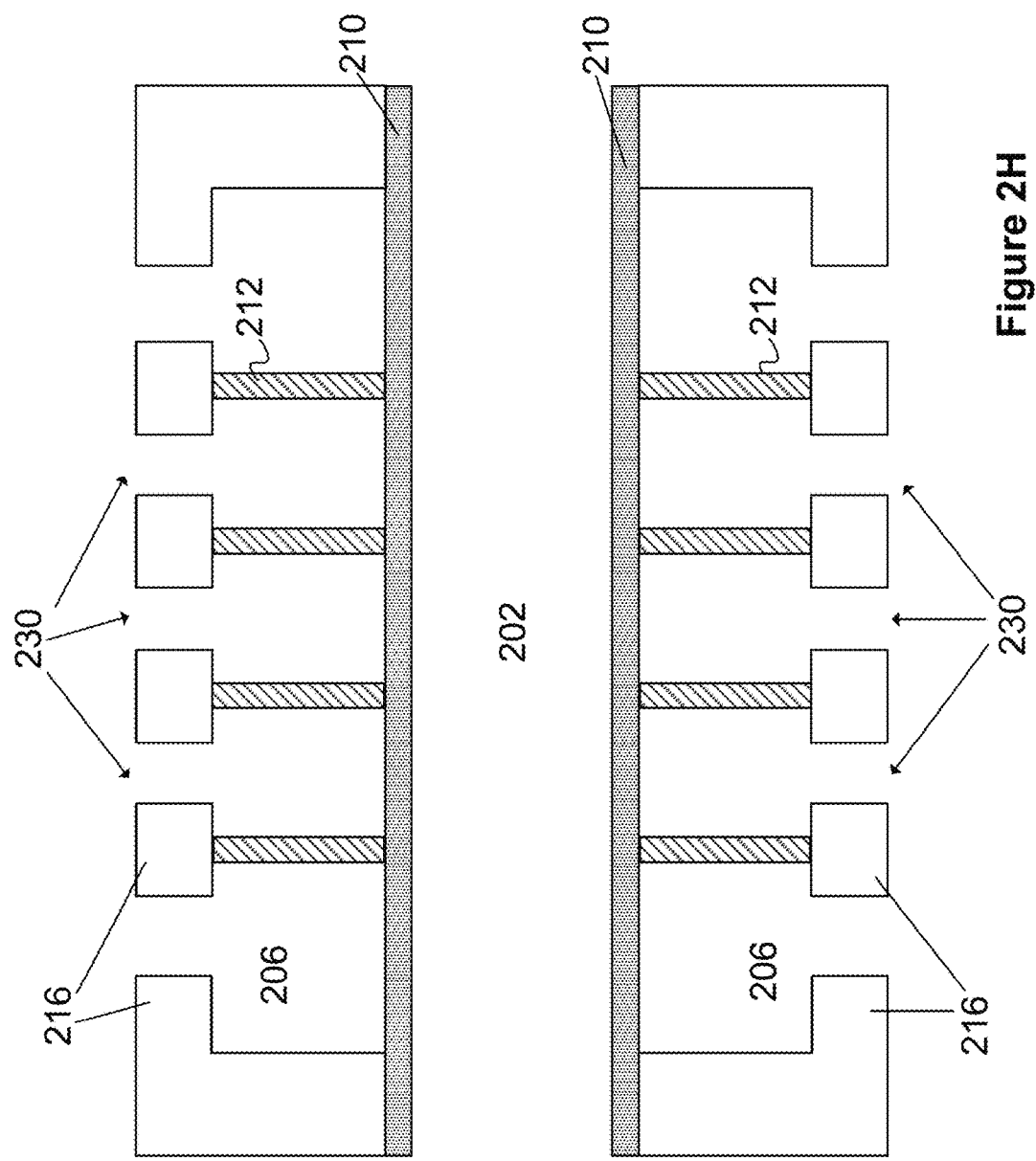

FIG. 2H shows the final step of the manufacturing process for manufacturing the device of FIG. 1A. The membranes 210 of the two instances of channel 206 (depicted in FIGS. 2E and 2F) are joined to the substrate walls 217 (depicted in FIG. 2G) to form the channel 202, which is defined on its upper and lower walls by the membranes 210, and on its sides by the substrate walls 217 as shown in FIG. 2G. The substrate walls 217 are not visible in the cross-sectional view of FIG. 2H. The channel 202 can be used as the blood flow channel of FIG. 1A, while the channels 206 can be used as the infusate channel and waste-collecting channel.

Figure 3:
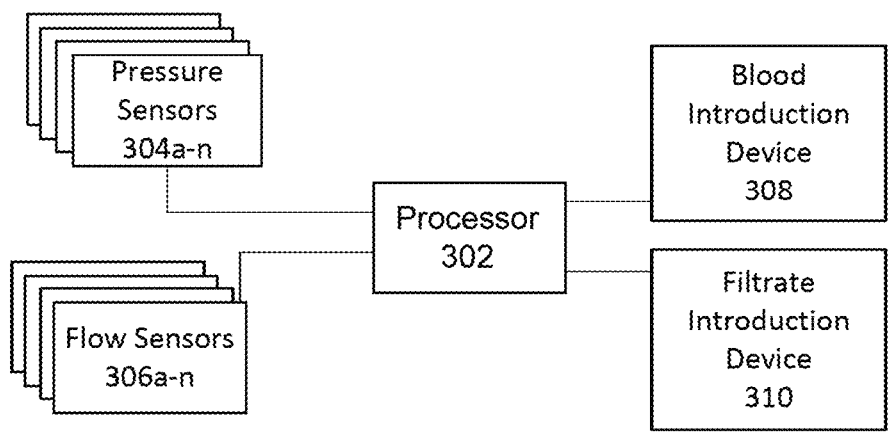
FIG. 3 is a block diagram of a control system that can be used with the devices of FIGS. 1A-1C, according to an illustrative implementation.

FIG. 3 depicts a block diagram of a control system 300 that can be used with the devices of FIGS. 1A-1C. The control system 300 includes an electronic processor 302 in communication with fluid pressure sensors 304, fluid flow sensors 306, a blood introduction device 308, and an infusate introduction device 310. Because the devices of FIGS. 1A-1C are intended for use in hemofiltration, promoting health of the patient's blood as it flows through the blood flow channel is essential. The control system 300 can be used to ensure that the patient's blood remains healthy.

Pressure sensors 304 and flow sensors 306 can be placed inside the blood flow channel. In some implementations, the physical shape of the fluid pressure sensors 304 and the flow sensors 306 can be selected to reduce interference with the flow of blood in the blood channel. For example, the pressure sensors 304 and the flow sensors 306 can have a small size or a hydrodynamic shape in order to promote laminar fluid flow. During operation of the device, the pressure sensors 304 and the flow sensors 306 can measure the pressure and flow characteristics in the blood flow channel and can transmit the measurements to the processor 302. The pressure sensors 304 and the flow sensors 306 can report measurements continuously, or at predetermined time intervals.

The processor 302 can determine whether the pressure and flow in the blood channel are suitable for maintaining blood health. The processor 302 can compare the measurements taken by the pressure sensors 304 and the flow sensors 306 to predetermined ranges that are deemed to be safe for blood. If the pressure or flow rate is outside of the acceptable range, the processor can attempt to correct the problem by transmitting signals to the blood introduction device 308 or the infusate introduction device 310. For example, the processor can reduce the flow rate in the blood channel by triggering the blood introduction device 308 (e.g., a pump) to decrease the amount of blood introduced at the inlet of the blood flow channels. The processor can also respond to an unacceptably high fluid pressure in the blood flow channel by triggering the infusate introduction device 310 to reduce the rate at which infusate is introduced at the inlets to the infusate channel. In another example, the processor can trigger the infusate introduction device 308 to increase the rate at which infusate is introduced (e.g., to increase the amount of convective clearance of toxins in the blood). In some implementations, the processor 302 can control the blood introduction device 308 and the infusate introduction device 310 to achieve a desired hematocrit profile in the blood channel. For example, the processor 302 can control the blood introduction device 308 and the infusate introduction device 310 to maintain a constant hematocrit level throughout the blood channel. Alternatively, in some implementations, the processor 302 can control the blood introduction device 308 and the infusate introduction device 310 to create a hematocrit profile that varies along the length of the blood channel.

Figure 4:
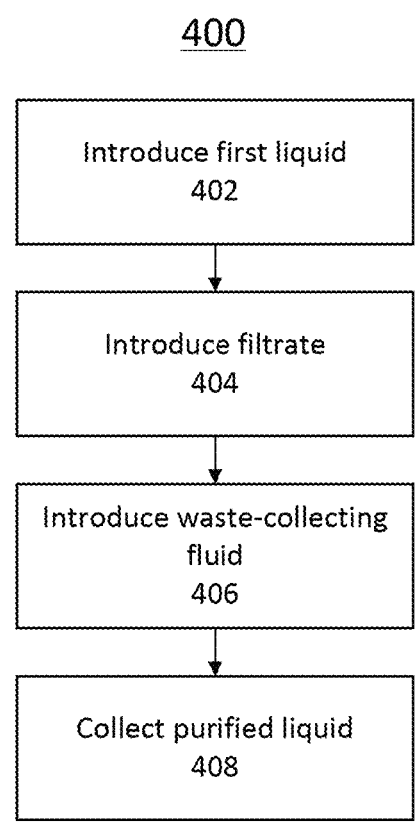
FIG. 4 is a flow diagram of a method for filtering liquid containing an analyte, according to an illustrative implementation.

FIG. 4 is a flow diagram of a method 400 for filtering liquid containing an analyte, according to an illustrative implementation. The method 400 includes the steps of introducing a first liquid solution (step 402), introducing infusate (step 404), introducing waste-collecting fluid (step 406), and collecting the cleansed liquid (step 408). In step 402, a first liquid containing an analyte is introduced into an inlet of one or more first channels. In some implementations, the fluid is blood that has been extracted from a patient for filtration. The analyte can be any undesirable substance, such as urea, uric acid, creatinine, or other toxins or pathogens. The first channels can have a height in the range of about 50 microns to about 500 microns, a width in the range of about 50 microns to about 900 microns, and a length in the range of about 3 centimeters to about 20 centimeters. If blood is to be introduced into the first channel, the first channel can include an anticoagulant coating on its inner walls and can be configured to maintain wall shear rates in the range of about 300 inverse seconds to about 3000 inverse seconds.

The method 400 includes the step of introducing infusate into an inlet of at least one second channel (step 404). The second channel is complementary to one or more of the first channels, and the infusate is introduced into the second channel such that it flows in a direction perpendicular to the direction of the first liquid in the first channel. The second channel is separated from the one or more complementary first channels by a first permeable membrane, which allows some of the infusate to be transported from the second channel into the first channel.

The method 400 includes the step of introducing waste-collecting fluid into an inlet of at least one third channel (step 406). The third channel is complementary to one or more of the first channels, and the third channel is separated from the one or more complementary first channels by a second permeable membrane, which allows some of the analyte to be transferred from the first channel to the third channel. In some implementations, introducing the first liquid (step 402), introducing the infusate (step 404), and introducing the waste-collecting fluid (step 406) can occur simultaneously and continuously. The waste-collecting fluid can be introduced such that the pressure in the third channel is less than the pressure in the adjacent first channel, which can result in an outflow of fluid form the first channel to the third channel.

In some implementations, introducing the first liquid (step 402), introducing the infusate (step 404), and introducing the waste-collecting fluid (step 406) can occur simultaneously and continuously. For example, the first liquid, infusate, and waste-collecting fluid can be flowed continuously through their respective channels. Infusate is transported from the second channel to the first channel through the first membrane. The infusion of infusate into the first channel causes an outflow of fluid from the first channel to the third channel through the second membrane. Waste particles, such as urea, uric acid, or creatinine, are also transported through the second membrane and into the third channel. The waste-collecting fluid in the third channel then carries the waste particles away from the first channel.

As discussed above, the first liquid can be blood that has been extracted from a patient for cleansing. The volume of liquid in the first channel can be substantially constant along its length so as to maintain substantially constant hematocrit in the blood. Blood health can also be preserved by maintaining laminar flow in the first channel and holding fluid shear rates in a range of about 300 to about 300 inverse seconds.

The method 400 can also include the step of collecting cleansed liquid from an outlet of the one or more first channels (step 408). As the liquid is transported along the length of the first channel from the inlet to the outlet, some of the waste particles in the liquid are removed from the first channel through the second membrane, as discussed above. Therefore, when the liquid reaches the outlet of the first channel, it has a substantially smaller concentration of waste particles. If the fluid is blood that has been extracted from a patient, the filtered blood can be collected at the outlet of the first channel and can then be returned to the patient.

What is claimed is:

1. A method for filtering a first liquid containing an analyte to provide a filtered liquid containing less analyte than the first liquid, the method comprising:

introducing, by a blood introduction device communicatively coupled to a processor, the first liquid into an inlet of one or more First Channels;

introducing, by a filtrate introduction device communicatively coupled to the processor, infusate into at least one Second Channel complementary to the one or more First Channels, such that at least some of the infusate flows from the at least one Second Channel through a first membrane and into the one or more First Channels, wherein the first liquid and the infusate are introduced such that the volume of fluid in each of the one or more First Channels is substantially constant along a length of the one or more First Channels, responsive to the processor controlling the blood introduction device and the filtrate introduction device to maintain the substantially constant volume of fluid along the length of the one or more First Channels;

introducing waste-collecting fluid into at least one Third Channel complementary to the one or more First Channels such that at least some of the analyte in the first liquid is transported through a second membrane into the at least one Third Channel, the at least one Third Channel including a first structural support to limit deformation of the second membrane; and collecting the filtered liquid from an outlet of one or more of the First Channels.

2. The method of claim 1, wherein introducing the first liquid comprises introducing blood.

3. The method of claim 2, wherein introducing the blood, the infusate, and the waste collecting fluid results in convective hemofiltration of the blood.

4. The method of claim 2, further comprising extracting the blood from a patient and returning filtered blood to the patient.

5. The method of claim 2, wherein the blood and the infusate are introduced such that hematocrit of the blood is substantially constant throughout the one or more First Channels.

6. The method of claim 2, further comprising controlling, by an operator, a hematocrit profile of the blood as it flows through the one or more First Channels.

7. The method of claim 2, wherein the blood is introduced such that a fluid shear rate in the one or more First Channels is within a range of about 300 inverse seconds to about 3000 inverse seconds.

8. The method of claim 1, wherein the first liquid and the infusate are introduced such that a pressure gradient across the first membrane is substantially constant along the length of the at least one Second Channels.

9. The method of claim 1, wherein the first liquid and the infusate are introduced such that fluid flow in the one or more First Channels is substantially laminar.

10. The method of claim 1, wherein the one or more First Channels include an anticoagulant coating on its walls.

11. The method of claim 1, wherein the first liquid and the infusate are introduced such that a pressure in the at least one Second Channel is greater than a pressure in the one or more First Channels, and the pressure in the one or more First Channels is greater than a pressure in the at least one Third Channel.

12. The method of claim 1, wherein each First Channel has a height in the range of about 50 microns to about 500 microns, a width in the range of about 50 microns to about 900 microns, and a length in the range of about 3 centimeters to about 20 centimeters.

13. The method of claim 1, wherein the introduction of the first liquid, the infusate, and the waste-collecting fluid results in a net infusion of fluid into the one or more First Channels from the at least one Second Channel and a net outflow of fluid from the one or more First Channels into the at least one Third Channel.

14. The method of claim 1, further comprising monitoring at least one of a pressure and flow rate of the first liquid as the first liquid flows through the one or more First Channels.

15. The method of claim 1, wherein the infusate is introduced into the at least one Second Channels in a direction perpendicular to a direction of fluid flow in the one or more First Channels.

16. The method of claim 1, comprising adjusting a flow rate of the infusate into the at least one Second Channels.

17. The method of claim 16, comprising measuring a pressure in the one or more First Channels, and wherein adjusting the flow rate of the infusate comprises adjusting the flow rate based on the measured pressure in the one or more First Channels.

18. The method of claim 17, wherein adjusting the pressure in the one or more First Channels comprises maintaining a pressure in the one or more First Channels suitable for maintaining blood health.

* * * * *